(12) United States Patent
Krause

(10) Patent No.: US 11,000,467 B2
(45) Date of Patent: May 11, 2021

(54) IN SITU CROSS-LINKABLE POLYSACCHARIDE COMPOSITIONS AND USES THEREOF

(71) Applicant: MERZ PHARMA GMBH & CO. KGAA, Frankfurt am Main (DE)

(72) Inventor: Andreas Krause, Frankfurt am Main (DE)

(73) Assignee: Merz Pharma GmbH & Co. KGaA, Frankfurt Am Main (DE)

( * ) Notice: Subject to any disclaimer, the term of this patent is extended or adjusted under 35 U.S.C. 154(b) by 180 days.

(21) Appl. No.: 15/768,442

(22) PCT Filed: Oct. 14, 2016

(86) PCT No.: PCT/EP2016/001710
§ 371 (c)(1),
(2) Date: Apr. 13, 2018

(87) PCT Pub. No.: WO2017/063749
PCT Pub. Date: Apr. 20, 2017

(65) Prior Publication Data
US 2018/0318203 A1    Nov. 8, 2018

(30) Foreign Application Priority Data
Oct. 16, 2015    (EP) .................... 15002953

(51) Int. Cl.
*A61K 8/73*    (2006.01)
*A61L 27/20*    (2006.01)
(Continued)

(52) U.S. Cl.
CPC .............. *A61K 8/735* (2013.01); *A61K 8/042* (2013.01); *A61K 9/0024* (2013.01);
(Continued)

(58) Field of Classification Search
None
See application file for complete search history.

(56) References Cited

U.S. PATENT DOCUMENTS

| 2006/0084759 | A1 | 4/2006 | Calabro et al. |
| 2012/0264913 | A1* | 10/2012 | Buffa .................. C08B 37/0072 530/345 |
| 2014/0105960 | A1* | 4/2014 | Zoldan ................ A61K 9/0024 424/450 |

FOREIGN PATENT DOCUMENTS

| EP | 2716662 A1 | 4/2014 |
| WO | 95/15168 A1 | 6/1995 |

(Continued)

OTHER PUBLICATIONS

Baier Leach J, Bivens KA, Patrick CW Jr, Schmidt CE. Photocrosslinked hyaluronic acid hydrogels: natural, biodegradable tissue engineering scaffolds. Biotechnol Bioeng; 82(5):578-589. (Year: 2003).*

(Continued)

*Primary Examiner* — Nicole P Babson
(74) *Attorney, Agent, or Firm* — McBee Moore & Vanik IP, LLC

(57) ABSTRACT

The present invention relates to a sterile in situ cross-linkable polysaccharide compositions for augmenting, filling or replacing soft tissues in various cosmetic and therapeutic applications. The composition comprises a first polysaccharide derivative functionalized with a nucleophilic group and a second polysaccharide derivative functionalized with an electrophilic group. Said nucleophilic and electrophilic functional groups spontaneously form in situ covalent linkages following co-injection in the body of a patient, resulting in the formation of a cross-linked hydrogel at the site of co-injection.

8 Claims, 2 Drawing Sheets
(2 of 2 Drawing Sheet(s) Filed in Color)

(51) Int. Cl.
| | |
|---|---|
| *A61K 8/04* | (2006.01) |
| *A61K 31/738* | (2006.01) |
| *A61L 27/52* | (2006.01) |
| *A61Q 19/08* | (2006.01) |
| *C08L 5/08* | (2006.01) |
| *A61K 47/36* | (2006.01) |
| *A61K 9/00* | (2006.01) |
| *C08B 37/08* | (2006.01) |
| *A61K 31/728* | (2006.01) |

(52) U.S. Cl.
CPC .......... *A61K 31/728* (2013.01); *A61K 31/738* (2013.01); *A61K 47/36* (2013.01); *A61L 27/20* (2013.01); *A61L 27/52* (2013.01); *A61Q 19/08* (2013.01); *C08B 37/0072* (2013.01); *C08L 5/08* (2013.01); *A61K 2800/594* (2013.01); *A61K 2800/87* (2013.01); *A61K 2800/88* (2013.01); *A61K 2800/882* (2013.01); *A61K 2800/91* (2013.01); *A61K 2800/95* (2013.01); *A61L 2400/06* (2013.01)

(56) References Cited

FOREIGN PATENT DOCUMENTS

| | | |
|---|---|---|
| WO | 00/016818 A1 | 3/2000 |
| WO | 01/40314 A1 | 6/2001 |
| WO | 2009/108100 A1 | 9/2009 |
| WO | 2011/069475 A2 | 6/2011 |
| WO | 2011/100469 A1 | 8/2011 |
| WO | 2012/113529 A1 | 8/2012 |

OTHER PUBLICATIONS

Hoyle, et al., "Thiol-click chemistry: a multifaceted toolbox for small molecule and polymer synthesis," Chem. Soc. Rev., (2010), vol. 39: 1355-1387.

Möller, et al., "Preparation and evaluation of hydrogel-composites from methacrylated hyaluronic acid, alginate, and gelatin for tissue engineering," Int. J. Artif. Organs, (2011), vol. 34, No. 2: 93-102.

Oommen, et al., "Smart Design of Stable Extracellular Matrix Mimetic Hydrogel: Synthesis, Characterization, and In Vitro and In Vivo Evaluation for Tissue Engineering," Adv. Funct. Mater., (2013), vol. 23: 1273-1280.

Ossipov, et al., "Functionalization of Hyaluronic Acid with Chemoselective Groups via a Disulfide-Based Protection Strategy for In Situ Formation of Mechanically Stable Hydrogels," Biomacromolecules, (2010), vol. 11: 2247-2254.

Shu, et al., "Disulfide Cross-Linked Hyaluronan Hydrogels," Biomacromolecules, (2002), vol. 3: 1304-1311.

Van Dijk, et al., "Synthesis and Applications of Biomedical and Pharmaceutical Polymers via Click Chemistry Methodologies," Bioconjugate Chem., (2009), vol. 20, No. 11: 2001-2016.

Varghese, et al., "In Situ Cross-Linkable High Molecular Weight Hyaluronan-Bisphosphonate Conjugate for Localized Delivery and Cell-Specific Targeting: A Hydrogel Linked Prodrug Approach," J. Am. Chem. Soc., (2009), vol. 131: 8781-8783.

Dahlmann, Julia et al., "Fully defined in situ cross-linkable alginate and hyaluronic acid hydrogels for myocardinal tissue engineering", Biomaterials, Nov. 7, 2012, pp. 940-951, vol. 34, No. 4.

Tan, Huaping et al., "Injectable in situ forming biodegradable chitosan-hyaluronic acid based hydrogels for cartilage tissue engineering", Biomaterials, May 1, 2009, pp. 2499-2506, vol. 30, No. 13, Elsevier Science Publishers BV, Barking, Great Britain.

Martinez-Sanz, Elena et al., "Bone reservoir: Injectable hylauronic acid hydrogel for minimal invasive bone augmentation", Journal of Controlled Release, Feb. 1, 2011, pp. 232-240, vol. 152, No. 2, Elsevier, Amsterdam, Netherlands.

Jia, Xinqiao et al., "Hyaluronic Acid-Based Microgels and Microgel Networks for Vocal Fold Regeneration", Biomacromolecules, Dec. 1, 2006, pp. 3336-3344, Retrieved from the Internet: URL: http://pubs.acs.org/doi/pdf/10.1021/bm0604956 [retrieved on Jan. 9, 2012].

Extended European Search Report of European Patent Application No. 15002953.6 dated Mar. 30, 2016.

International Search Report of International Patent Application No. PCT/EP2016/001710 dated Nov. 30, 2016.

* cited by examiner

IN SITU CROSS-LINKABLE POLYSACCHARIDE COMPOSITIONS AND USES THEREOF

CROSS-REFERENCE TO RELATED APPLICATIONS

This application is a National Stage entry of International Application No. PCT/EP2016/001710, filed 14 Oct. 2016, which claims priority to European Patent Application No. 15002953.6, filed 16 Oct. 2015.

FIELD OF THE INVENTION

The present invention relates to a sterile in situ cross-linkable polysaccharide compositions for augmenting, filling or replacing soft tissues in various cosmetic and therapeutic applications. The composition comprises a first polysaccharide derivative functionalized with a nucleophilic group and a second polysaccharide derivative functionalized with an electrophilic group. Said nucleophilic and electrophilic functional groups spontaneously form in situ covalent linkages following co-injection in the body of a patient, resulting in the formation of a cross-linked hydrogel at the site of co-injection.

BACKGROUND OF THE INVENTION

Injectable fillers are today used in numerous therapeutic and cosmetic applications for adding volume to soft tissues. In aesthetic medicine, dermal fillers are increasingly used for the rejuvenation of the face and selected areas of the body. They allow enhancement of facial features (e.g., cheeks and lips), reduction of wrinkles (e.g., nasolabial folds) and creases, and can restore some of the lost volume and elasticity of the skin and underlying tissues that occurs with ageing. This makes the skin look smoother and fuller and, thus, provides a more youthful appearance.

A wide variety of materials are known for use in soft tissue fillers. Most of these materials have a temporary effect (about three to eighteen months) because they are resorbed in the body (e.g., collagen, hyaluronic acid (HA), calcium hydroxylapatite (CaHA) and poly-L-lactic acid (PLLA)). There are also a few permanent (i.e. non-absorbable) fillers, such as an FDA-approved filler material that is based on polymethylmethacrylate beads (PMMA microspheres). Some soft tissue fillers also contain lidocaine (a local anesthetic agent), which is intended to decrease pain or discomfort related to the injection.

Today, the most commonly used material in soft tissue fillers worldwide is hyaluronic acid (HA). This is due to its excellent ability to create volume and favorable safety profile. HA is a naturally occurring glycosaminoglycan present in the extracellular matrix of, e.g., the dermis and is composed of alternating residues of β-D-(1→3) glucuronic acid (GlcUA) and β-D-(1→4)-N-acetylglucosamine (GlcNAc). HA is able to combine with water and swell when in gel form, causing a smoothing/filling effect. In most cases, HA used in dermal fillers is crosslinked to make it last longer in the body (about six to eighteen months).

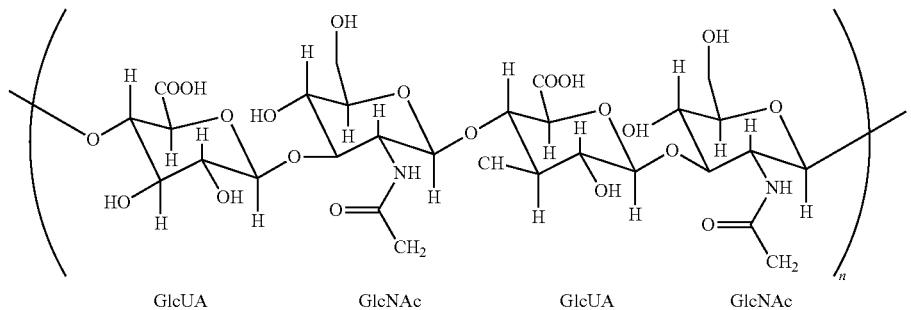

Various crosslinking approaches for covalently binding the polymer chains of polysaccharides (e.g., HA) molecules together to form a filler material matrix with inter- and intramolecular cross-links are known in the art. A widely used approach is chemical crosslinking with chemical agents. These agents commonly react with the polysaccharide's hydroxyl and/or carboxyl functional groups. Commonly used cross-linking agents include, without limitation, DVS (divinylsulfone), di- or multi-functional epoxides (e.g., 1,4-butanediol diglycidyl ether (BDDE), 1,2-bis(2,3-epoxypropoxy)ethylene (EGDGE) and 1,2,7,8-diepoxyoctane (DEO)), PEG-based crosslinking agents (e.g., pentaerythritol tetraglycidyl ether (PETGE)), biscarbodiimides (BCDI) (e.g., phenylenebis-(ethyl)-carbodiimide and 1,6-hexamethylenebis-(ethylcarbodiimide)), di-amine or multiamine cross-linkers (e.g., hexamethylenediamine (HMDA) and 3-[3-(3-aminopropoxy)-2,2-bis(3-amino-propoxymethyl)-propoxy]-propylamine (4 AA)), bis(sulfosuccinimidyl)suberate (BS), 1-(2,3-epoxypropyl)-2,3-epoxycyclohexane, epichlorohydrin, aldehydes (e.g., formaldehyde and glutaraldehyde), and hydrazides (bis-, tris- and polyvalent hydrazide compounds, e.g., adipic dihydrazide (ADH)).

Other methods that have been employed for cross-linking of injectable polysaccharide hydrogels include photochemical cross-linking of methacrylated polymers (Möller et al., Int. J. Artif. Organs 2011, 34:93-102), Michael addition cross-linking (Shu et al., Biomacromolecules 2002, 3:1304-1311), Schiff-base reaction cross-linking (Tan et al., Biomaterials 2009, 30:2499-2506), "click" chemistry approaches using reactions like the thiol-ene reaction or the azide-alkyne cycloaddition (Hoyle et al., Chem. Soc. Rev. 2010, 39:1355-1387; van Dijk et al., Bioconjug. Chem. 2009, 20:2001-2016). Polysaccharide-based photocrosslinked fillers for augmenting soft tissue are also known in the art (see, e.g., US 2011/069475). In addition, the esterification of carboxyl functions of acid polysaccharides with hydroxyl groups of the same or different polysaccharide molecule, thereby forming "inner" inter- and/or intramolecular ester-based cross-links (referred to as "autocross-linked polymer" or "ACP") has been investigated in the art. Furthermore, US 2006/0084759 describes a tyramine-modified and crosslinked HA hydrogel material, wherein cross-linking is achieved via peroxidase-mediated dityramine-linkages that can be performed in vivo.

Conventional pre-formed hydrogels, however, often suffer from the drawback that they are too viscous to be injected through fine needles. Therefore, many efforts have been made to develop in situ gelling hydrogel compositions suited for different applications. These compositions are injected in the tissue in liquid form rather than in the form of a pre-formed gel. For example, WO 95/15168 describes the synthesis of HA hydrazide derivatives by employing EDC (1-ethyl-3-(3-dimethylaminopropyl)carbodiimide) coupling chemistry. The hydrazide-HA may be cross-linked with homo- or heterodifunctional or Traut's cross-linking agents to form a hydrogel for drug delivery. WO 00/016818 discloses the in situ formation of a hydrogel by cross-linking an aldehyde- or amine-functionalized derivative of HA (e.g., adipic dihydrazido-HA) with a homo- or heterobifunctional cross-linker (e.g., a bifunctional N-hydroxysuccinimide ester cross-linker such as $(SPA)_1$-PEG).

Furthermore, WO 01/40314 discloses a hydrogel composition comprising an oxidized polysaccharide, e.g., an alginate polymer with aldehyde groups (PAG), and at least one cross-linking agent having two or more functional groups capable of reversibly cross-linking the polysaccharide in the hydrogel system, such as an adipic acid dihydrazide (ADH) cross-linking agent. Further, WO 2011/100469 discloses a cross-linked HA hydrogel for use as a vitreous substitute biomaterial made by reacting oxidized HA bearing aldehyde functional groups (oxi-HA) with a dihydrazide cross-linker, e.g., adipic acid dihydrazide (ADH).

In addition, WO 2009/108100 discloses a HA-based hydrogel prepared in situ by mixing aldehyde-modified HA and a hydrazide-modified polyvinyl-alcohol (PVAH) cross-linking reagent to form a cross-linking structure that exhibits a plurality of hydroxyl groups. WO 2011/069475 discloses a method for preparing an aldehyde-HA derivative containing an aldehyde group by oxidation of the primary hydroxyl group at C6 of the glucosamine repeat unit using a TEMPO (2,2,6,6-tetramethyl-piperidinyloxyl)/co-oxidant system, and the use of said aldehyde-HA derivative for preparing crosslinked HA hydrogels by reacting with a diamine compound (e.g., hexanediamine) or amine-HA (e.g., hexanediamine substituted HA).

Dahlmann et al. (Biomaterials 2013, 34:940-951) describes fully defined in situ cross-linkable alginate and HA hydrogels for myocardial tissue engineering. The hydrogels are prepared by reacting aldehyde and hydrazide functionalized alginate and HA in the presence of human type I collagen and neonatal rat heart cells (NRHC) to yield a hydrazone cross-linked hydrogel-based bioartificial cardiac tissue.

Ossipov et al. (Biomacromolecules 2010, 11:2247-2254) discloses the synthesis of hydrazide functionalized HA using a specific symmetrical di-functional reagent having a central divalent protecting group that can undergo an amide-type reaction with the carboxylate residue of HA in aqueous solution. The hydrazide functionalized HA can be used for the in situ formation of a hydrazone HA hydrogel by mixing with an aldehyde HA derivative. The resulting hydrogel is suited for use as a growth factor delivery vehicle for tissue engineering applications.

Varghese et al. (J. Am. Chem. Soc. 2009, 131:8781-8783) reports on a HA derivative that is dually-functionalized with a hydrazide group and an aminomethylene bisphosphonate group capable of covalently binding bisphosphonate (BP; an antiosteoclastic and antineoplastic small molecule drug). Mixing of said dually functionalized HA with aldehyde functionalized HA results in the in situ formation of an injectable HA hydrogel for the controlled release of the BP drug at the site of implantation.

Oommen et al. (Adv. Funct. Mater 2013, 323:1273-1280) describes a HA hydrogel prepared by mixing a HA-aldehyde derivative with a carbodihydrazide (CDH) functionalized HA derivative to obtain a HA hydrogel with hydrazone bonds. It is further described that the in situ HA hydrogel formation in the presence of a therapeutic protein (e.g., the recombinant human growth factor BMP-2) afforded a hydrogel for in vivo applications that is capable of delivering growth factors for bone tissue regeneration.

For many clinical uses, in situ cross-linkable polysaccharide hydrogels are desirable since they can be easily injected even through a fine needle, which helps in better controlling the rate of injection and improves the handling of the syringe. In addition, in situ cross-linkable polysaccharide hydrogels can be formed into any complex shapes and then subsequently cross-linked, are easily mixable with bioactive agents and/or cells, and adhere to a given tissue during gel formation.

However, the existing in situ cross-linkable hydrogel compositions are not satisfactory in that they do not exhibit one or more properties desired or required for the intended purpose. Generally, an in situ cross-linkable hydrogel composition should be biocompatible, non-immunogenic, non-inflammatory and safe. It should neither react with biological components of the surrounding tissues nor generate harmful by-products, and efficiently cross-link in situ following administration. Also, it should be bio-degradable but at the same time provide a sufficiently long in vivo persistence. Furthermore, and importantly, an in situ cross-linkable hydrogels should be injectable through a fine needle which, however, requires that the viscosity of the injected in situ cross-linkable hydrogel composition is sufficiently low.

OBJECT OF THE INVENTION

In view of the above, the object of the present invention is to provide an in situ cross-linkable composition, which can be easily extruded through fine needles and after administration forms in situ a cross-linked hydrogel with desired properties (e.g., in terms of mechanical, chemical, rheological, biological and immunological properties) for augmenting, filling or replacing soft tissues in various cosmetic and therapeutic applications.

SUMMARY OF THE INVENTION

The above object is solved by the provision of two functionalized polysaccharide derivatives, which spontaneously form covalent cross-links following injection in the body of a patient (i.e. under in vivo conditions). The thus formed in situ cross-linked polysaccharide network in the form of a hydrogel acts as a soft tissue filler, e.g. a dermal filler. The in situ cross-linkable polysaccharide composition of the present invention is advantageous in that the two functionalized polysaccharide derivatives can be co-injected in liquid form, thereby enabling co-injection with low extrusion forces even through fine needles. Desirably, the in situ gel formation does not generate any harmful by-products. The only by-product is water that is readily absorbed by the formed hydrogel and/or the surrounding tissues. In addition, the in situ formed hydrogel has the desired properties in terms of tissue integration, skin improvement, tissue shaping capacity and volumizing ability.

In a first aspect, the present invention relates to the use of a first polysaccharide derivative and a second polysaccharide derivative for the in situ formation of a cross-linked hydrogel in cosmetic applications, wherein the first polysaccharide derivative is functionalized with a nucleophilic group and the second polysaccharide derivative is functionalized with an electrophilic group, and both the first and second polysaccharide derivatives are sterilized, and wherein the nucleophilic group and the electrophilic group form a covalent linkage in situ following co-injection of the first and second polysaccharide derivatives to a target site in the body of a patient, resulting in the formation of a cross-linked hydrogel at the target site.

In another aspect, the present invention provides a first polysaccharide derivative, preferably in the form of a first precursor solution, and a second polysaccharide derivative, preferably in the form of a second precursor solution, as defined herein for the in situ formation of a cross-linked hydrogel in therapeutic applications. The therapeutic applications or indications include, but are not limited to, stress urinary incontinence, vaginal dryness, vesico-ureteral reflux, vocal fold insufficiency, and vocal fold medialization.

In a further aspect, the present invention provides a combination of a first hyaluronic acid (HA) derivative and a second hyaluronic acid (HA) derivative as defined herein, preferably in the form of a first precursor solution that comprises the first hyaluronic acid (HA) derivative and a second precursor solution that comprises the second hyaluronic acid (HA) derivative.

In a yet further aspect, the present invention provides a multi-barrel syringe system prefilled with at least (a) a first precursor solution, comprising a first polysaccharide derivative as defined herein, in one barrel and (b) a second precursor solution, comprising a second polysaccharide derivative as defined herein, in another barrel.

In still another aspect, the present invention provides a kit for the in situ formation of a cross-linked polysaccharide hydrogel, comprising (i) a first container comprising a first precursor solution of a first polysaccharide derivative as defined herein and (ii) a second container comprising a second precursor solution of a second polysaccharide derivative as defined herein and, optionally, (iii) instructions for use.

In yet another aspect, the present invention provides a method for the in situ formation of a cross-linked polysaccharide hydrogel in cosmetic or therapeutic applications, comprising the steps of:

(a) providing a first precursor solution of a first polysaccharide derivative and, separately thereof, a second precursor solution of a second polysaccharide derivative, wherein the first polysaccharide derivative is functionalized with a nucleophilic group and the second polysaccharide derivative is functionalized with an electrophilic group, and both the first and second precursor solutions are sterilized, (b) mixing the first precursor solution and the second precursor solution into a in situ cross-linkable mixed solution, and (c) injecting the mixed solution to a target site in the body of a patient, wherein the nucleophilic group of the first polysaccharide derivative and the electrophilic group of the second polysaccharide derivative form a covalent linkage in situ to result in the formation of a cross-linked hydrogel at the target site.

Particular embodiments of the present invention are set forth in the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A set of photographs is herewith submitted.

Figure 1:
Figure 2:
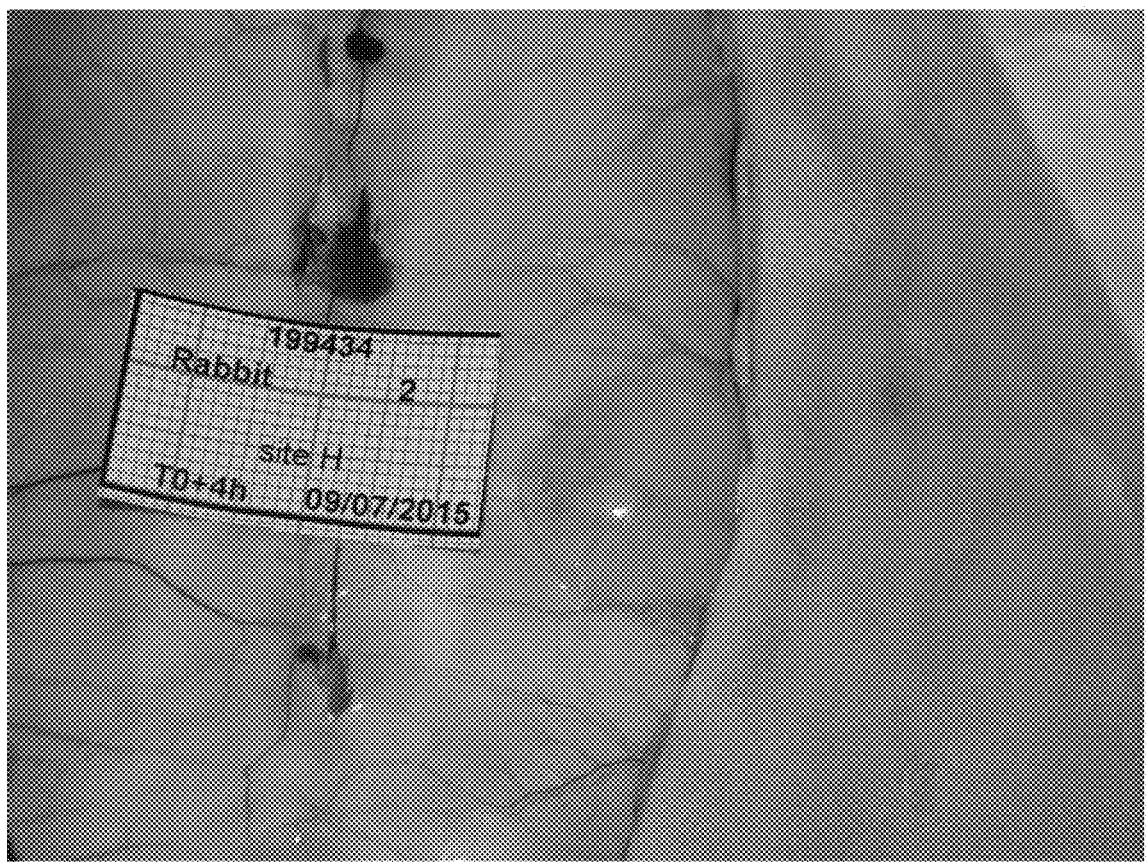

For a more complete understanding of the present invention, reference is made to the following description and accompanying drawings, in which:

FIG. 1 is a picture showing the trapezoid bulk filling in the skin of test rabbit 1 formed by the in vivo gelled test article 1 at t=0 h following intradermal injection of 200 μL as one tunnel (site D; upper left), two tunnels (site I; upper right) and as four bolus (site J; lower right). The PBS control (200 μL) is injected in site E (lower left); and FIG. 2 is a macroscopic picture showing the bulge formed by test article 2 at t=4 h following subdermal injection of 1000 μL in rabbit 2 after opening of the skin.

DETAILED DESCRIPTION OF THE INVENTION

The sterile in situ cross-linkable polysaccharide composition of the present invention is easily injectable through thin needles with low injection forces and provides skin improvement, skin shaping or good volumizing effect. More specifically, the in situ cross-linkable composition can be conveniently applied to the target tissue by injection in the form of a sterile low viscosity liquid mixture generated concomitantly with injection by simple physical mixing of two sterile precursor solutions, each precursor solution containing a different functionalized polysaccharide derivative. This advantageously allows the use of fine needles which in turn enhances patient comfort (reduced pain upon injection, lowered back pressure) and further enables the practitioner to accurately and safely (no vessel clogging) inject the hydrogel into the desired target sites, such as various layers of the skin.

Moreover, the injected mixture of the precursor solutions rapidly and efficiently cross-links in situ to form a covalently cross-linked hydrogel at the target site in the body. No additives, no catalysts, no pH switch, no UV irradiation nor any other external stimuli (or "triggers") are required to induce the cross-linking reaction. In particular, no cross-linker is used or required. The only by-product generated by the cross-linking reaction is typically water that is readily absorbed by the hydrogel and/or the surrounding tissues. Furthermore, the functionalized polysaccharide derivatives of the present invention can be synthesized in a relatively simple manner, usually in a single step reaction and, advantageously, can be conveniently sterilized by moist heat sterilization (e.g., steam sterilization, preferably autoclaving).

Furthermore, the in situ formed cross-linked hydrogel exhibits favorable mechanical, chemical and rheological properties for use as a soft tissue filler material. In particular, it has a high capacity to create volume. Also, the in situ cross-linked hydrogel of the present invention has a prolonged in vivo residence time while still being bio-degradable. In addition, it can be desirably include anesthetics (e.g., lidocaine) and a variety of other components (e.g., cells, including stem cells and adipocytes, fat, lipids, growth factors and vitamins). Therefore, the in situ cross-linkable composition of the present invention is particularly suited for use as a dermal filler for cosmetic (aesthetic) purposes.

In a first aspect, the present invention concerns the use of a first polysaccharide derivative and a second polysaccharide derivative for the in situ formation of a cross-linked hydrogel in cosmetic applications. The first polysaccharide derivative is functionalized with a nucleophilic group and the second polysaccharide derivative is functionalized with an electrophilic group. Further, both the first and second polysaccharide derivatives are sterilized. The nucleophilic group and the electrophilic group form a covalent linkage in situ following co-injection of the first and second polysaccharide derivatives to a target site in the body of a patient, resulting in the formation of a cross-linked hydrogel at the target site.

As used herein, the term "in situ" means at the site of administration. Thus, in order to form a hydrogel at the site of administration, the first and second polysaccharide derivatives are generally co-injected or otherwise applied together to a specific site (target site) within a patient's body, e.g., a site in need of tissue augmentation for aesthetic reasons, and allowed to covalently crosslink at the site of co-injection. Within the present invention, the terms "in situ" and "in vivo" may be interchangeably used. A "patient" in the sense of the present invention may be any individual or subject, e.g., a mammal and, preferably, a human, in need of a treatment of a particular condition, state or disease, e.g., for cosmetic (aesthetic) or therapeutic purposes.

Within the context of the present invention, the term "co-injection" generally means that the first polysaccharide derivative and the second polysaccharide derivative are injected together as a single liquid composition, e.g., solution, to a target site in the body of a patient. The term "injectable" or "injection", as used herein, indicates that the in situ hydrogel forming composition can be dispensed from a syringe or a syringe system. In particular, the term "co-injection" preferably means that the first polysaccharide derivative and the second polysaccharide derivative are mixed, in particular homogeneously mixed, prior to exiting from the tip of the needle and entering the target site in the body of a patient, and then injected as a mixture to a target site in the body of a patient. Within the present invention, the terms "injection" or "co-injection" may refer to intra-, inter- or subdermal injection or subcutaneous injection. Further, the term "needle", as used herein, is intended to comprise or be synonymous to a "cannula" or any other needle-like objects suitable for injection.

The term "hydrogel", as used herein, means a water-swollen three-dimensional network consisting of covalently cross-linked polymer chains. Preferably, the in situ cross-linked (or "gelled") hydrogel is cohesive. The term "cohesive" or "cohesivity" within the meaning of the present invention is defined as the capacity of a material (e.g., of a hydrogel) not to dissociate, because of the affinity of its molecules for each other. Cohesivity is a key characteristics of gel implants (e.g., the in situ gelled hydrogels described herein) and considered necessary for the solid and fluid phases of a gel to remain intact, and thus for gel integrity. In the context of the present invention, cohesivity of a polysaccharide hydrogel, in particular of a HA-based hydrogel, can be determined using the Gavard-Sundaram Cohesivity Scale (Sundaram et al., Plast. Reconstr. Surg. 136:678-686, 2015).

The term "spontaneous" or "spontaneously", as used herein, is intended to refer to the fact that the nucleophilic group of the first polysaccharide derivative and the electrophilic group of the second polysaccharide derivative form a covalent linkage under in vivo conditions, i.e. after co-injection to a target site in the body of a patient, without any external stimuli (also referred to as "triggers") like heat or UV light, resulting in the in situ formation of a cross-linked polysaccharide hydrogel at the target site.

Within the present invention, an in situ (or in vivo) formed hydrogel is generally suitable for, is used as, and/or functions as a soft tissue filler. The term "soft tissue filler", as used herein, generally refers to a material designed to add volume to areas of soft tissue deficiency. This includes, e.g. augmenting, filling or replacing soft tissues. Herein, the term "soft tissue" generally relates to tissues that connect, support, or surround other structures and organs of the body. Soft tissues include, for example, muscles, tendons (bands of fiber that connect muscles to bones), fibrous tissues, fat, blood vessels, nerves, and synovial tissues (tissues around joints). In the context of the present invention, the soft tissue filler is preferably a dermal filler.

The term "derivative", as used herein, preferably refers to a polysaccharide that has been functionalized with a nucleophilic group or a electrophilic group and is suited for the purpose of in situ (or in vivo) formation of a crosslinked polysaccharide hydrogel at the site of administration in the body of a patient. Preferably, the functionalized polysaccharide derivatives of the present invention contain no other chemical modification than a nucleophilic group or an electrophilic group.

The first and second polysaccharide derivatives are usually both sterilized. The term "sterilized" or "sterile", as used herein, is intended to refer to heat sterilization, in particular moist heat sterilization (e.g., steam sterilization), and preferably refers to autoclaving. Autoclaving may be carried out at a temperature of 120° C. to 132° C. for 0.3 min to 20 min, or at 121° C. to 130° C. for 0.5 min to 10 min, e.g. at 121° C. for 0.5 min to 2 min.

Preferably, the first polysaccharide derivative is present in the form of a first sterile precursor solution and the second polysaccharide derivative is preferably present in the form of a second sterile precursor solution.

The first and second sterile precursor solutions typically have a low complex viscosity of 0.001 Pa·s to 5.0 Pa·s, in particular 0.005 Pa·s to 3.0 Pa·s, preferably 0.001 Pa·s to 1.0 Pa·s, more preferably 0.001 Pa·s to 0.1 Pa·s, as determined by oscillatory rheological measurements at 1 Hz and 25° C. Furthermore, the first and second precursor solutions may both be characterized by a low extrusion force of from 0.01 N to 15 N, preferably 0.1 N to 10 N, more preferably 0.5 N to 7.5 N, and most preferably 0.01 N to 50 N or 1.0 N to 5.0 N, as measured through a 30 G needle (TSK Laboratory) at an extrusion rate of about 0.21 mm/sec using a standard 1.0 ml glass syringe (BD Hypak SCF, 1 ml long RF-PRTC, ISO 11040, inner diameter of 6.35 mm).

In accordance with the present invention, the first and second polysaccharide derivatives are mixed in the course of co-injection to form a liquid in situ cross-linkable composition comprising a mixture of the first and second polysaccharide derivatives. Usually, both the first polysaccharide derivative and the second polysaccharide derivative are present as separate first precursor solution and second precursor solution, respectively. Mixing of these two precursor solutions during injection (or "co-injection") yields the liquid in situ cross-linkable composition that ultimately exits the needle and is implanted in the body.

The liquid in situ cross-linkable composition preferably has a complex viscosity of 0.1 Pa·s to 100 Pa·s or 0.1 Pa·s to 75 Pa·s or 1.0 Pa·s to 75 Pa·s, more preferably from 1 Pa·s to 50 Pa·s or from 5 Pa·s to 50 Pa·s, when measured as described above. Furthermore, the injection force of the composition is preferably 0.01 N to 20 N or 0.01 to 10 N, more preferably 0.1 N to 10 N, and most preferably 1.0 N to 5.0 N, when measured as described above.

The mixing and injection (or "co-injection") may be achieved using a double-barrel syringe as described herein below or any other suitable syringe system in which the first and second polysaccharide derivatives are physically separated prior to simultaneous extrusion and concomitant mixing and co-injection of the mixed first and second polysaccharide derivatives through a needle (cannula) in the body of a patient. Thus, the co-injection should be as fast as to avoid preliminary cross-linking prior to deposition of the first and second polysaccharide derivatives at the target site in the body. On the other hand, the gelling time should be reasonably short in order to avoid spreading of the co-injected material into surrounding tissues.

The amount of the first polysaccharide derivative present in the first precursor solution may be from 0.1 wt. % to 5.0 wt. %, preferably from 0.5 wt. % to 4.0 wt. %, more preferably from 1.0 wt. % to 3.0 wt. %, and most preferably from 1.5 wt. % to 2.5 wt. %, and the amount of the second polysaccharide derivative present in the second precursor solution may be from 0.1 wt. % to 5.0 wt. %, preferably from 0.5 wt. % to 4.0 wt. %, more preferably from 1.0 wt. % to 3.0 wt. %, and most preferably from 1.5 wt. % to 2.5 wt. %. Moreover, the weight ratio of the co-injected first and second polysaccharide derivative is preferably from 15:85 to 85:15, more preferably from 30:70 to 70:30, and most preferably 40:60 to 60:40 or 50:50 (first derivative to second derivative).

Furthermore, the first and/or second precursor solutions may comprise additional substances such as cells, including stem cells and adipocytes, fat, lipids, growth factors, cytokines, drugs, and bioactive substances. More specifically, the first and/or second precursor solutions may comprise local anesthetic agents, polyalcohols, vitamins, alkali metal and alkaline earth metal salts, metals, antioxidants, amino acids, and ceramic particles.

Within the context of the present invention, the addition of a local anesthetic is particularly desirable in view of its ability to mitigate pain upon injection. Exemplary local anesthetic agents include, but are not limited to, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclomine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octocaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and salts thereof.

Preferably, the anesthetic agent is lidocaine, such as in the form of lidocaine HCl. The first and/or second precursor solutions may have a lidocaine concentration of, for example, 0.05 wt. % to 8.0 wt. %, 0.1 wt. % to 4.0 wt. %, 0.2 wt. % to 3.0 wt. %, 0.3 wt. % to 2.0 wt. %, or 0.4 wt. % to 1.0 wt. %.

Suitable polyols for use herein include, but are not limited to, glycerol, mannitol, sorbitol, propylene glycol, erythritol, xylitol, maltitol, and lactitol. Particularly suitable for use herein is mannitol and glycerol. Further, the polyol is preferably glycol, optionally in combination with one or more of the aforementioned polyol compounds, in particular mannitol. Suitable vitamins include vitamin C, vitamin E and vitamins of the B group, i.e. one or more of $B_1$, $B_2$, $B_3$, $B_5$, $B_6$, $B_7$, $B_9$ and $B_{12}$ vitamins. The vitamins may be present to stimulate and maintain cellular metabolism and, thus, to promote collagen production. Particularly preferred for use here is vitamin C, vitamin E and vitamin $B_6$. A preferred salt for use in the soft tissue filler composition is a zinc salt. The ceramic particles are preferably hydroxyapatite particles, e.g., calcium hydroxyl apatite (CaHA) particles.

Within the present invention, the electrophilic group is preferably an aldehyde moiety, and the nucleophilic group may be selected from an amino, aminooxy, carbazate or hydrazide moiety, and is preferably a hydrazide moiety. The term "aldehyde moiety", as used herein, includes an aldehyde functional group (i.e. —CHO are "formyl") or any group or residue having a pendant —CHO functional group, in particular an aldehyde (i.e. —CHO)-terminated group (e.g., a linear or branched $C_1$-$C_6$ alkyl or alkenyl group with a terminal —CHO group).

The aldehyde functionalized polysaccharide derivative for use in the present invention has preferably intact, cyclic polysaccharide rings. This means that the aldehyde functionalized polysaccharide derivative does not have any oxidized open rings of the saccharide units within the polysaccharide (also referred to as "linearized" saccharide units). Thus, according to this preferred embodiment, any method for preparing an aldehyde functionalized polysaccharide derivative is suitable for use herein, provided it does not lead to ring-opening of the cyclic saccharide units of the polysaccharides. Accordingly, the often used method of the prior art for introducing aldehyde groups into polysaccharides by oxidation of vicinal diols within the monomeric saccharide units by the use of periodate (e.g., $NaIO_4$) is preferably not used and is preferably excluded from the present invention.

The term "hydrazide moiety", as used herein, includes a hydrazide functional group and hydrazide-terminated groups or residues, usually having no more than a total number of carbon atoms of 15, 10, 5, 4, 3 or 2. The hydrazide moiety is preferably hydrazide (i.e. [polysaccharide]-C(O)—NH—$NH_2$) or a dihydrazide moiety, particularly a dihydrazide moiety of general formula

[polysaccharide]-C(=O)—NH—NH—$R^1$—C(=O)—NH—$NH_2$ wherein $R^1$=a covalent bond, C(=O), C(=O)—O—$R^2$, (C=O)—$R^2$, wherein $R^2$=linear or branched $C_1$, $C_2$, $C_3$, $C_4$, $C_5$ or $C_6$ alkyl or alkenyl group. Particularly preferred for use herein is carbodihydrazide (CDH). If CDH is used as hydrazide moiety and coupled with the carboxyl group of a polysaccharide, the resultant modified polysaccharide has the following pendant hydrazide-terminated moiety: polysaccharide-C(=O)—R, wherein R is NH—NH—C(=O)—NH—$NH_2$.

The polysaccharide of the first and second polysaccharide derivatives may be selected from natural polysaccharides and semi-synthetic polysaccharides. Specific examples of suitable carboxylic polysaccharides include carboxylated cellulose and carboxylated cellulose derivatives (e.g., carboxymethylcellulose, carboxyethylcellulose, carboxymethylethylcellulose), carboxymethyldextran, carboxymethylstarch, alginate, hyaluronic acid, pectin, chitin, chondroitin sulfate, dermatan sulfate, heparin, heparin sulfate, heparosan, and the like.

Preferably, the first polysaccharide derivative is based on hyaluronic acid, alginate, heparosan, heparin or heparin sulfate, and the second polysaccharide derivative is preferably based on hyaluronic acid, cellulose, chitosan, chitin, or heparosan. Particularly preferred, both the first polysaccharide derivative and the second polysaccharide derivative are based on hyaluronic acid or, alternatively based on heparosan, or the first polysaccharide derivative is based on heparosan and the second polysaccharide derivative is based on hyaluronic acid, or the first polysaccharide derivative is based on hyaluronic acid and the second polysaccharide derivative is based on heparosan.

In accordance with a preferred aspect of the present invention, the first polysaccharide derivative is a (first) hydrazide functionalized hyaluronic acid (HA) derivative and the second polysaccharide derivative is a (second) aldehyde functionalized hyaluronic acid (HA) derivative. Upon in situ crosslinking, the hydrazide functionalized HA derivative and the aldehyde functionalized HA derivative form a hydrazone crosslinked hyaluronic acid (HA) hydrogel.

All definitions, explanations and descriptions provided above with regard to the use of first and second "polysaccharide" derivative also apply for the first and second hyaluronic acid (HA) derivatives, unless otherwise stated. Furthermore, any specific reference to hyaluronic acid or HA may also include heparosan. In other words, throughout the present application, the term "hyaluronic acid" or "HA" may include "heparosan" or may be replaced by "heparosan".

The hydrazide moiety of the hydrazide functionalized hyaluronic acid (HA) derivative and the aldehyde moiety of the aldehyde functionalized hyaluronic acid (HA) derivative are preferably defined as herein above. Thus, the hydrazide moiety is preferably hydrazide or a dihydrazide group or residue, in particular a carbodihydrazide (CDH) as defined above. Preferably, the first HA derivative is functionalized with a hydrazide moiety at a carboxyl group of a saccharide unit of HA.

The modification of the carboxyl groups may be carried out by any method known in the art using a water soluble coupling reagent. For example, a suitable method involves the use of standard carbodiimide chemistry, such as the use of EDC (1-ethyl-3-(3-dimethylaminopropyl) carbodiimide) as coupling reagent, for coupling the hydrazide-terminated moiety with the carboxyl group to form the corresponding HA acyl hydrazides (see, e.g., WO 95/15168). Other usable coupling reagents are triazine compounds such as DMTMM (4-(4,6-dimethoxy-1,3,5-triazin-2-yl)-4-methylmorpholinium chloride; see, e.g., WO 2016/097211), active esters such as N,N'-disuccinimidyl carbonate, and tetramethyl aminium salts (e.g., HATU).

The second HA derivative is preferably functionalized with an aldehyde moiety without breaking the cyclic saccharide rings, e.g. without linearizing the HA backbone. Such linearized saccharide units are generated, e.g., by classical periodate oxidation which results in the introduction of aldehyde groups into the cyclic ring structure of the saccharide units of HA and, thus, concomitantly results in the breakage and "linearization" of the backbone of HA. For further details, reference is made to the corresponding explanations set forth above, which equally apply here.

Preferably, the second HA derivative is made by conversion of a —$CH_2OH$ group into a —CHO group and, particularly, the aldehyde functionalized HA derivative is preferably modified in that the hydroxyl group at C6 of the N-acetylglucosamine unit of HA is oxidized to result in a formyl (—CHO) functional group. A suitable method for the later modification is described, e.g., in WO 2011/069475 using TEMPO (2,2,6,6-tetramethyl-1-piperidinyloxy) as an oxidant to convert a primary alcohol group into an aldehyde.

The liquid in situ cross-linkable HA composition that enters the body of a patient, i.e. the mixture of the two precursor solutions, preferably contains a total amount of hydrazide and aldehyde functionalized HA derivatives of from 0.1 wt. % to 5.0 wt. %, and/or the weight ratio of the hydrazide functionalized HA derivative to the aldehyde functionalized HA derivative is preferably in the range of 15:85 to 85:15. With respect to preferred ranges of said total amount and said weight ratio, it is referred to the comments set out above in respect of polysaccharides, which equally apply to hyaluronic acid as a preferred polysaccharide.

In accordance with the present invention, the total amount of hydrazide and aldehyde functionalized HA derivatives present in the liquid composition is preferably from 0.1 wt. % to 5.0 wt. %, in particular from 0.5 wt. % to 4.0 wt. %, more preferably from 1.0 wt. % to 3.0 wt. %, and most preferably from 1.5 wt. % to 2.5 wt. %. Further, the weight ratio of the hydrazide functionalized HA derivative to the aldehyde functionalized HA derivative is preferably from 15:85 to 75:25, more preferably from 25:75 to 60:40, particularly preferably from 40:60 to 60:40, and is most preferably 50:50.

The hydrazide functionalized HA derivative and the aldehyde functionalized HA derivative, independently from each, is made of or based on a HA starting material having an average molecular weight of from $3.0 \times 10^4$ to $5.0 \times 10^6$ Da, more preferably $0.1 \times 10^6$ to $4.0 \times 10^6$ Da, and most preferably from $0.3 \times 10^6$ to $3.0 \times 10^6$ Da or from $0.5 \times 10^6$ to $2.0 \times 10^6$ Da. As used herein, the term "hyaluronic acid" or "HA" includes hyaluronic acid, hyaluronate, and any hyaluronate salt such as sodium hyaluronate.

The first and/or second precursor solutions may further comprise uncross-linked HA, the uncross-linked HA preferentially having a molecular weight of between $5.0 \times 10^5$ and $4.0 \times 10^6$ Da, preferably between $1.0 \times 10^6$ Da to $3.0 \times 10^6$ Da. The weight ratio of the cross-linked HA to the uncross-linked HA may be between 1:1 and 1:0.001, in particular between 1:0.5 and 1:0.005 or 1:0.1 to 1:0.01.

The degree of modification of the hydrazide functionalized HA derivative and the aldehyde functionalized HA derivative, expressed as the ratio of the sum of hydrazide moieties or aldehyde moieties to the sum of HA disaccharide units may be, independently from each other, in the range of from 0.1% to 50%, preferably from 0.5% to 25%, from 0.5% to 15% or from 0.5% to 5.0%. The degree of modification may be determined via spectrometry and/or spectroscopy analytical methods, such as NMR, UV—VIS and IR, titration, HPLC, SEC, viscosity, among others. Conveniently, the degree of modification may be determined by $^1$H-NMR.

All numbers herein expressing "molecular weight", "molecular mass", "mean molecular weight" or "mean molecular mass" of polysaccharides (e.g. HA) are to be understood as indicating the mass-average molar mass (or mass-average molecular mass) or $M_w$ (w is for weight; also referred to as weight-average molecular weight (WAMW)) in Daltons (Da). The mass-average molar mass ($M_w$) is defined as follows: $M_w = \Sigma_i N_i M_i^2 / \Sigma_i N_i M_i$, wherein $N_i$ is the number of molecules of molecular mass $M_i$.

Various methods can be applied herein to determine the molecular weight of HA, such as intrinsic viscosity measurements (e.g., European Pharmacopoeia 7.0—Hyaluronic Acid monograph No. 1472, January 2011), capillary electrophoresis (CE) (e.g., according to Kinoshita et al., Biomed. Chromatogr., 2002, 16:141-45), gel permeation chromatography (GPC) (e.g., according to Kim et al., Food Chem., 2008, 109:63-770), and multi-angle laser light scattering combined with size-exclusion chromatography (SEC-MALLS) (e.g., in accordance to Hokputsa et al., Eur. Biophys. J. Biophys. Lett., 2003, 32:450-456).

Within the framework of the present invention, the mass-average molar mass ($M_w$) of HA polymers is preferably determined by gel permeation chromatography (GPC) or viscometry via the Mark-Houwink equation. The GPC technique involves forcing a polymer solution through a matrix of crosslinked polymer particles at a pressure of up to several hundred bar. As well known to a skilled person, the use of low dispersity standards allows one to correlate retention time with molecular mass.

The mass-average molar mass ($M_w$) determined by means of the Mark-Houwink equation may also be referred to the viscosity average molar mass or $M_v$. The Mark-Houwink equation gives a relation between intrinsic viscosity ($\eta$) and molecular weight M and allows determination of the molecular weight of a polymer from data on the intrinsic viscosity and vice versa. Within the context of the present invention, the intrinsic viscosity is preferably measured according to the procedure defined in European Pharmacopoeia 7.0 (Hyaluronic Acid monograph No. 1472, January 2011). For calculation of the molecular weight of HA from intrinsic viscosity data, the following Mark-Houwink equation is used herein:

$$[\eta]=K \times M^a,$$

wherein [$\eta$]=intrinsic viscosity in m$^3$/kg, M=molecular weight, K=2.26×10$^{-5}$, and a=0.796.

In accordance with the present invention, the cosmetic applications may include, but are not limited to, the treatment of wrinkles and lines of the skin, glabellar lines, nasolabial folds, chin folds, marionette lines, jawlines, buccal commissures, perioral wrinkles, crow's feet, cutaneous depressions, scars, temples, subdermal support of the brows, malar and buccal fat pads, tear troughs, nose, lips, cheeks, chin, perioral region, infraorbital region, and facial asymmetries.

Therapeutic applications targeted by the present invention include, but are not limited to, the treatment of stress urinary incontinence, vaginal dryness, vesico-ureteral reflux, vocal fold insufficiency, and vocal fold medialization.

In a further aspect, the present invention relates to a combination of a first hyaluronic acid (HA) derivative and a second hyaluronic acid (HA) derivative as defined herein, wherein the first HA derivative is functionalized with a hydrazide moiety and the second HA derivative is functionalized with an aldehyde moiety, and wherein said hydrazide moiety and said aldehyde moiety are capable of forming a covalent linkage in situ, e.g. under in vivo conditions.

Preferably, the first hyaluronic acid (HA) derivative is in the form of a first precursor solution and the second hyaluronic acid (HA) derivative is in the form of a second precursor solution.

The hydrazide functionalized HA derivative, the aldehyde functionalized HA derivative, the first and second sterile precursor solutions, and the in situ formation of a hydrazone cross-linked hyaluronic acid (HA) hydrogel may be further defined as defined herein above.

In a yet further aspect, the present invention relates to a multi-barrel syringe system for the in situ formation of cross-linked polysaccharide hydrogel, wherein the multi-barrel syringe is prefilled with at least (a) a first precursor solution of a first polysaccharide derivative functionalized with a nucleophilic group as described herein in one barrel and (b) a second precursor solution of a second polysaccharide derivative functionalized with an electrophilic group as described herein in another (i.e. separate) barrel. Both the first and second precursor solutions are, as described above, sterile.

Specifically, the present invention relates to a multi-barrel syringe system, preferably a double-barrel or triple-barrel system, prefilled with at least (a) a first (sterile) precursor solution of a first polysaccharide derivative functionalized with a nucleophilic group as defined herein in one barrel and (b) a second (sterile) precursor solution of a second polysaccharide derivative functionalized with an electrophilic group as defined herein in another (separate) barrel, and optionally, a solution with additional components (e.g., fatt, fatty acids, stem cells, vitamins, polyols, mineral salts, anesthetic agents such as lidocaine, antioxidants, amino acids, alkali metal and alkaline earth metal salts) in an optionally present third barrel. Preferably, the syringe system is a double-barrel syringe system prefilled with (a) a first precursor solution as defined herein and (b) a second precursor solution as defined herein in the other barrel.

The first and second polysaccharide derivatives, the nucleophilic and electrophilic groups, the first and second sterile precursor solutions and the in situ formed cross-linked polysaccharide hydrogel may be further defined as defined herein above. Furthermore, the multi-barrel syringe system, including the double-barrel syringe system, is suitable for use in cosmetic or therapeutic applications, in particular replacing or filling of a biological tissue or increasing the volume of a biological tissue for the purpose of cosmetic or therapeutic applications, as defined herein or, particularly preferred, for use as a dermal filler in aesthetic uses.

The term "multi-barrel system", as used herein, is intended to mean any system or device, usually a syringe, which comprises at least two separate barrels and may have two or more plungers. The term "double-barrel syringe system", as used herein, is intended to mean any system or device, usually a syringe, which comprises two separate barrels and may have one or two plungers. In addition, the multi-barrel, e.g. double-barrel, syringe system generally comprises a tip cap, or a needle or cannula with or without a needle shield, in order to seal the end(s) of the syringe system. The barrels generally have the storage capacity for containing enough of the first and second precursor solutions. The barrels may be made of glass, plastic or any other suitable material and may have different geometries, inner diameters, material compositions, clearness, etc. Further, the multi-barrel syringe system may be a double-barrel syringe system in the form of a syringe having two integrally connected syringes, i.e. two integrally connected barrels, and a mono or double plunger assembly for dispensing the contents from the barrels. Also, the syringe system may include two detachably connected barrels and two or one detachably connected plungers.

Furthermore, the syringe system may also include means (e.g., an applicator tip) configured for thoroughly mixing the components contained in the barrels before being dispensed through the applicator tip. Thus, the barrels are generally connected, and the plunger assembly is generally configured, to dispense the contents from the barrels simultaneously, such that the appropriate mixing ratios of the precursor solutions will be preserved.

Preferably, the multi-barrel syringe system, including the double-barrel syringe system, is for the in situ formation of a hydrazone cross-linked hyaluronic acid (HA) hydrogel, wherein the double-barrel syringe is prefilled with (a) a first precursor solution of a hydrazide functionalized hyaluronic acid (HA) derivative in one barrel and (b) a second precursor solution of an aldehyde functionalized HA derivative in another separate barrel. The hydrazide functionalized HA derivative, the aldehyde functionalized HA derivative, the first and second sterile precursor solutions, and the in situ formation of a hydrazone cross-linked hyaluronic acid (HA) hydrogel are preferably as defined herein above.

In still another aspect, the present invention relates to a kit for the in situ formation of a cross-linked polysaccharide hydrogel, comprising (i) a first container comprising a first sterile precursor solution of a first polysaccharide derivative as defined herein that is functionalized with a nucleophilic group and (ii) a second container comprising a second sterile precursor solution of a second polysaccharide derivative as defined herein that is functionalized with an electrophilic group and, optionally, (iii) instructions for use.

The first and second polysaccharide derivatives, the nucleophilic and electrophilic groups, the first and second sterile precursor solutions and the in situ formed cross-linked polysaccharide hydrogel may be further defined as defined herein above. The term "container", as used herein, is not particularly limited and includes, for example, glass or plastic bottles, vials, carpules, or any other sealed container.

The "instructions for use" are preferably instructions for use in cosmetic or therapeutic applications, in particular replacing or filling of a biological tissue or increasing the volume of a biological tissue for the purpose of cosmetic or therapeutic applications, as defined herein or, particularly preferred, instructions for use as a dermal filler in aesthetic uses.

Preferably, the kit is for the in situ formation of a hydrazone cross-linked hyaluronic acid (HA) hydrogel, comprising a (i) a first container comprising a first sterile precursor solution of a hydrazide functionalized HA derivative and (ii) a second container comprising a second sterile precursor solution of an aldehyde functionalized HA and, optionally, (iii) instructions for use. The hydrazide functionalized HA derivative, the aldehyde functionalized HA derivative, the first and second sterile precursor solutions, and the in situ formation of a hydrazone cross-linked hyaluronic acid (HA) hydrogel may be further defined as defined herein above, particularly as defined in relation to the first aspect of the present invention. Optionally, the kit may comprise a third sterile solution comprising additional components as those mentioned in connection with the multi-barrel syringe system.

In yet another aspect, the present invention provides a method for the in situ formation of a cross-linked hydrogel in cosmetic or therapeutic applications, comprising the steps of:
 (a) providing a first precursor solution of a first polysaccharide derivative and, separately thereof, a second precursor solution of a second polysaccharide derivative, wherein the first polysaccharide derivative is functionalized with a nucleophilic group and the second polysaccharide derivative is functionalized with an electrophilic group, and both the first and second precursor solutions are sterilized,
 (b) mixing the first precursor solution and the second precursor solution into a in situ cross-linkable mixed solution, and
 (c) injecting the mixed solution to a target site in the body of a patient, wherein the nucleophilic group of the first polysaccharide derivative and the electrophilic group of the second polysaccharide derivative form a covalent linkage in situ to result in the formation of a cross-linked hydrogel at the target site.

The mixing and injection may be carried out using a syringe system as defined herein, usually enabling a, preferably homogeneous, physical mixing of both components (i.e. the first and second precursor compositions) before being dispensed form the needle (cannula). The term "homogeneous", as used herein, means uniformly mixed, dispersed or diluted throughout the mixture, dispersion or solution, or refers to a material of uniform structure and/or composition throughout.

The present invention will now be further illustrated by the following, non-limiting examples.

EXAMPLES

The examples provided below illustrate the preparation of an in situ cross-linkable hyaluronic acid (HA) hydrogel and show in animal tests that the hydrogel is a promising filler material for various cosmetic and therapeutic applications. In addition, the examples demonstrate that the in situ cross-linkable HA composition can be easily injected through fine needles without exerting undue force, while still providing the desirable mechanical and rheological properties (i.e. complex viscosity ($\eta^*$), storage modulus (G'), loss modulus (G"), and loss tangent (tan δ)) for augmenting biological tissues.

Measurement of Extrusion Force

Extrusion force (injection force) was measured by means of a texture analyzer (TA.XTPlus, Texture Technologies, Corp.) equipped with a 1.0 ml glass syringe (BD Hypak SCF, 1 ml long RF-PRTC, ISO 11040, inner diameter of 6.35 mm) and a 30 G needle (TSK Laboratory). The extrusion force was measured using a test speed of 0.21 mm/sec over a distance of 25 mm (target mode: distance; force: 100.0 g). Pre-test and post-test speeds were 0.21 mm/sec and 10.0 mm/sec, respectively. The trigger force was 2.0 g (trigger type: auto (force)) and the strain was 10.0%. The averaged force after reaching a plateau was taken as the extrusion force.

Measurement of Complex Viscosity ($\eta^*$) and Storage and Loss Moduli (G' and G")

The complex viscosity ($\eta^*$) and the storage and loss moduli (G' and G") were measured at 25° C. using a rheometer (Anton Paar Physica MCR 302 Rheometer, Anton Paar GmbH) equipped with a cone-plate geometry (50 mm diameter, 0.1° angle, CP50-1, gap size 0.1 mm). The samples were oscillated at a stress of 1 Pa and the oscillation frequency was varied from 0.1 to 10 Hz.

In the examples below, the term "equivalent" or "eq." as used herein refers to hyaluronic acid disaccharide repeat units, if not indicated otherwise. The percentages are weight percentages, if not indicated otherwise.

Example 1

Synthesis of HA-Aldehyde Derivative (HA-Ald)

The aldehyde-functionalized HA derivative was prepared by selective oxidation of the primary C6 hydroxyl group of the N-Acetylglucosamine (GlcNAc) unit of HA in accordance with the method described in WO 2011/069475 (see, e.g., Example 1). In brief, hyaluronic acid (HA) (Mw=1.0× $10^6$ Da) was oxidized using the TEMPO/co-oxidant system (TEMPO, 2,2,6,6-tetramethyl-1-piperidinyloxy). After dialysis, the solution was lyophilized to yield aldehyde-functionalized HA (in the following referred to as "HA-Ald").

Example 2

Synthesis of HA-Hydrazide Derivative (HA-Hyd)

HA (6000.0 mg, 14.9 mmol of disaccharide repeat units) was dissolved in 700.0 mL deionized water at room temperature for 12 h. HOBt (2289.3 mg, 14.9 mmol) was added and thereafter solid EDC (1-ethyl-3-(3-dimethylaminopropyl) carbodiimide (1428.9 mg, 7.84 mmol) was added. The pH was adjusted to 5.5 to 6.5, and the solution was stirred for 1 h. Next, carbohydrazide (CDH; 4043.5 mg, 44.88 mmol) was added, and stirring was continued for 10 h at room temperature.

The solution was then precipitated in 5.0 L isopropanol, and the precipitate was collected, solubilized in saline and loaded into a dialysis bag (Spectra Por-6, MWCO 3500). The precipitate was dialyzed against distilled water containing 0.1 M NaCl (2×2 L, 48 h), then dialyzed against saline (2×2 L, 24 h). Finally, the solution was lyophilized to yield 5000 mg to 5500 mg HA-hydrazide derivative (in the following referred to as "HA-Hyd").

Example 3

HA Hydrogel Formation and Characterization

HA hydrogels were prepared at room temperature (about 25° C.) by mixing equal amounts of steam sterilized (131° C., 0.7 min) HA-aldehyde derivative of Example 1 ("HA-Ald") and steam sterilized (131° C., 0.7 min) HA-hydrazide derivative of Example 2 ("HA-Hyd"). The HA-Ald and HA-Hyd derivatives were dissolved separately in sterile PBS, pH 6.5 to 7.5, each at a concentration of 15 mg/ml and 24.5 mg/ml, respectively. Then, 1.0 ml of each of the HA-Ald and HA-Hyd precursor solutions (separately for each of the 15 mg/ml and 24.5 mg/ml concentrations) was loaded into a 1 ml Luer-lock syringe with a volume ratio of 1:1. The two syringes used were each connected at each tip to a Y-connector to enable effective mixing of the two precursor solutions simultaneously with extrusion through the needle.

The measured average extrusion force, and rheological properties ($\eta^*$, G', G" and tan($\delta$)) of the sterile precursor solutions and of the mixture of the sterile precursor solutions are shown in Table 1.

As can be seen from Table 1, the extrusion force and the complex viscosity of both the HA-Hyd precursor solution and the HA-Ald precursor solution are very low, indicative of the liquid (non-gel) state of the precursor solutions. Furthermore, the mixture of the two precursor solutions was found to have an extrusion force of only about 5 N, which is approximately the sum of each precursor solution (15 mg/ml) immediately after extrusion from separate syringes through a fine needle of 30 G. Accordingly, the mixed precursor solution is much more easily injected as compared to a dermal filler composition in the form of a pre-formed hydrogel.

In situ cross-linked HA hydrogels were prepared on petri dishes from the 15 mg/ml and 24.5 mg/ml precursor solutions, respectively, indicated in Table 1. As adequate and sufficient duration of cross-linking to obtain the final gel state, a period of about 30 min was determined by rheology. The rheological properties ($\eta^*$, G', G" and tan($\delta$)) of the hydrogels were thus assessed 30 min after mixing the two precursor solutions using an Anton Paar rheometer as described above. The results are shown in Table 2.

TABLE 2

Rheological properties ($\eta^*$, G', G" and tan($\delta$)) of two HA hydrogels varying in their HA-Hyd and HA-Ald concentrations

| Hydrogel | $\eta^*$ (Pa · s) | G' (1 Hz; Pa) | G" (1 Hz; Pa) | tan($\delta$) (G"/G') | Cohesivity GS-Scale[1] |
|---|---|---|---|---|---|
| HA hydrogel prepared by mixing (1:1 v/v) HA-Hyd precursor solution (15 mg/ml) and HA-Ald precursor solution (15 mg/ml) | 8.8 | 54 | 8.6 | 0.16 | 3 |
| HA hydrogel prepared by mixing (1:1 v/v) HA-Hyd precursor solution (24.5 mg/ml) and HA-Ald precursor solution (24.5 mg/ml) | 44 | 276 | 33 | 0.12 | 4 |

[1]Sundaram et al., Cohesivity of Hyaluronic Acid Fillers: Development and Clinical Implications of a Novel Assay, Pilot Validation with a Five-Point Grading Scale, and Evaluation of Six U.S. Food and Drug Administration-Approved Fillers, Plast. Reconstr. Surg. 136: 678-686, 2015

As shown in Table 2, the in situ cross-linkable hydrogel exhibits rheological properties that are comparable to other commercially available fillers that are pre-formed and then

TABLE 1

Extrusion force and rheological properties ($\eta^*$, G', G" and tan ($\delta$)) of the sterile precursor solutions and the mixture of precursor solutions

| Precursor solution/mixture | Conc. [mg/ml] | Extrusion force [N] | $\eta^*$ [Pa · s] | G' (1 Hz) | G" (1 Hz) | tan ($\delta$) (G"/G') |
|---|---|---|---|---|---|---|
| HA-Hyd | 10.0 | 0.8 ± 0.05 | 0.007 | 0.002 | 0.04 | 2.0 |
| HA-Hyd | 15.0 | 1.3 ± 0.1 | 0.01 | 0.02 | 0.07 | 3.2 |
| HA-Hyd | 30.0 | 3.9 ± 0.5 | 0.06 | 0.08 | 0.41 | 4.8 |
| HA-Ald | 10.0 | 1.7 ± 0.2 | 0.023 | 0.006 | 0.14 | 21.8 |
| HA-Ald | 15.0 | 4.0 ± 0.2 | 0.38 | 0.25 | 2.4 | 9.3 |
| HA-Ald | 30.0 | 9.3 ± 0.3 | 0.99 | 1.16 | 6.11 | 5.2 |
| Mixture (1:1 v/v) of HA-Hyd precursor solution (15 mg/ml HA-Hyd) and HA-Ald precursor solution (15 mg/ml HA-Ald) | 15 | 5.1 ± 0.3 | 8.7 | 54.4 | 8.6 | 0.16 |
| Mixture (1:1 v/v) of HA-Hyd precursor solution (24.5 mg/ml HA-Hyd) and HA-Ald precursor solution (24.5 mg/ml HA-Ald) | n.d.[1] | n.d.[1] | 44.2 | 275.8 | 33.3 | 0.12 | injected into a patient. In addition, the tested in situ cross-linkable hydrogels are both cohesive, as indicated by a score of equal to or higher than 3 on the Gavard-Sundaram Cohesivity Scale.

Example 4

Animal Testing to Establish Proof-of-Concept

Preliminary Animal Study

The two formulations given in Table 2 were used for the in vivo formation of hydrogels in rabbits. The first hydrogel ("Test article 1") was generated by co-injecting (1:1 v/v) HA-Hyd precursor solution (15 mg/ml) and HA-Ald precursor solution (15 mg/ml) into the rabbit skin. The second hydrogel ("Test article 2") was generated by co-injecting (1:1 v/v) HA-Hyd precursor solution (24.5 mg/ml) and HA-Ald precursor solution (24.5 mg/ml) into the rabbit skin.

Depending on the injection depth, a volume of 100 µL to 1000 µL was injected in different skin layers of the rabbits by intradermal (ID) and subdermal (SD) injections, and compared to two marketed dermal fillers (Control article 1: Belotero Balance; Control article 2: Belotero Volume). Phosphate-buffered saline (PBS) was used as negative control. The results are shown in FIGS. 1 and 2.

As can be seen from FIG. 1, Test article 1 appears as roughly trapezoid bulk in the dermis after intradermal injection, as classically encountered with HA-based fillers. In addition, as can also be seen, the type of injection (i.e. bolus, one tunnel and two tunnels injections) does not result in any morphologic differences. Essentially the same results were found for Test article 2. Moreover, additional tests have shown that intradermal injection of different volumes of Test articles 1 and 2 does not lead to relevant differences in the test article distribution (results not shown).

FIG. 2 is a macroscopic picture of a "bulge" or "bleb" formed by the in vivo cross-linked Test article 2 at t=4 h. As can be seen, Test article 2 provides a lifting effect several hours after injection. In comparison, a saline solution has completely disappeared within that time. The same was observed with Test article 1. The bleb obtained after in vivo cross-linking is similar to the bleb obtained after injection of fillers having rheological profiles similar to that of pre-formed commercial fillers (e.g., the Belotero® filler range (Merz Aesthetics)).

In conclusion, intradermal and subdermal injections of variable amounts of test articles 1 and 2 provided the desired lifting effect and were not associated with any adverse histopathologic effects in the rabbit skin.

Follow-Up 12-Weeks Animal Study

A 12-weeks study was carried out in rabbits to determine the severity of skin reactions after intradermal injection (ID) of the above-mentioned Test article 1 and subcutaneous injection (SC) of the above-mentioned Test article 2. The responses were compared to ID injected Control article 1 (Belotero Balance) and SC injected Control article 2 (Belotero Volume Lidocaine). Four weeks after injections, sites were macroscopically observed and histopathologically analyzed to evaluate the skin reactions of each article. All the sites were macroscopically observed after injection, then daily during five days, and then weekly until termination.

Surprisingly, it was found that the two test articles (in vivo HA filler) formed very small granules and spicules which were infiltrating between the dermal collagen fibers. The control articles (Belotero Balance and Belotero Balance Lidocaine) formed larger granules and lakes which were filling large spaces in the dermis, and not infiltrating the dermal collagen. In other words, the in vivo HA filler achieved a substantially better infiltration of the tissue as Belotero Balance (full tissue integration versus local filling) although Belotero Balance is known for its excellent tissue integration ability (Flynn et al., Comparative histology of intradermal implantation of mono and biphasic hyaluronic acid fillers, Dermatol Surg. 2011, 37:637-643; and Micheels et al., Superficial dermal injection of hyaluronic acid soft tissue fillers: comparative ultrasound study, Dermatol Surg. 2012, 38:1162-1169).

In summary, the 12-weeks study in rabbits showed the comparability of the in vivo HA filler of the present invention to commercial dermal fillers. It further showed that the in vivo HA filler provides unique characteristics such as an improved tissue infiltration which results in a full tissue integration as opposed to a local filling. These results strongly suggests the potential of the in vivo HA filler of the present invention for augmenting, filling or replacing soft tissues in various cosmetic and therapeutic applications.

The invention claimed is:

1. A method for the in situ formation of a cross-linked hydrogel, comprising:
    (a) providing a first precursor solution of a first polysaccharide derivative and, separately thereof, a second precursor solution of a second polysaccharide derivative, wherein the first polysaccharide derivative is functionalized with a nucleophilic group and the second polysaccharide derivative is functionalized with an electrophilic group, and both the first and second precursor solutions are sterilized,
    (b) mixing the first precursor solution and the second precursor solution into an in situ cross-linkable mixed solution, and
    (c) injecting the in situ cross-linkable mixed solution to a target site in a body of a patient, wherein the nucleophilic group of the first polysaccharide derivative and the electrophilic group of the second polysaccharide derivative form a covalent linkage in situ to result in the formation of a cross-linked hydrogel at the target site,
    wherein the first polysaccharide derivative is a hydrazide functionalized first hyaluronic acid (HA) derivative and the second polysaccharide derivative is an aldehyde functionalized second hyaluronic acid (HA) derivative, and the first HA derivative is functionalized with a hydrazide moiety at a carboxyl group of a saccharide unit of HA wherein said hydrazide moiety is hydrazide or carbodihydrazide, and the second HA derivative is functionalized with an aldehyde moiety made by conversion of a —$CH_2OH$ group into a —CHO group,
    and wherein the cross-linked hydrogel is used in a cosmetic application.

2. The method of claim 1, wherein the in situ formation of a covalent linkage occurs spontaneously upon co-injection and/or wherein the in situ formation of a covalent linkage results in the release of no other by-product than water.

3. The method of claim 1, wherein the sterilized first and second precursor solutions each have a complex viscosity of 0.001 Pa·s to 5.0 Pa·s, as determined by oscillatory rheological measurements at 1 Hz and 25° C., or have each an injection force of from 0.01 N to 15 N, as measured through a 30 G needle at an extrusion rate of 0.21 mm/sec using a 1.0 ml glass syringe, or both.

4. The method of claim 1, wherein the first precursor solution and the second precursor solution are mixed during co-injection but prior to entering the body of the patient to form a liquid in situ cross-linkable composition.

5. The method of claim 4, wherein said liquid in situ cross-linkable composition has a complex viscosity of 0.1 Pa·s to 100 Pa·s, as determined by oscillatory rheological measurements at 1 Hz and 25° C., or has an injection force of 0.01 N to 20 N, as measured through a 30 G needle at an extrusion rate of 0.21 mm/sec using a 1.0 ml glass syringe, or both.

6. The method of claim 1, wherein concentration of the first polysaccharide derivative present in the first precursor solution is from 0.1 wt. % to 5.0 wt. %, and the concentration of the second polysaccharide derivative present in the second precursor solution is from 0.1 wt. % to 5.0 wt. %, and/or wherein a weight ratio of the first polysaccharide derivative to the second polysaccharide derivative comprised in the in situ cross-linkable composition that is injected to a target site in the body of the patient is from 15:85 to 85:15.

7. The method of claim 1, wherein said cosmetic application comprises treatment of wrinkles or lines of the skin, glabellar lines, nasolabial folds, chin folds, marionette lines, jawlines, buccal commissures, perioral wrinkles, crow's feet, cutaneous depressions, scars, temples, subdermal support of brows, malar or buccal fat pads, tear troughs, nose, lips, cheeks, chin, perioral region, infraorbital region, or facial asymmetries.

8. A method of augmenting, filling, or replacing soft tissue in cosmetic applications comprising injecting a cross-linked hydrogel to a target site in a body of a patient, wherein the cross-linked hydrogel is produced by:

(a) providing a first precursor solution of a first polysaccharide derivative and, separately thereof, a second precursor solution of a second polysaccharide derivative, wherein the first polysaccharide derivative is functionalized with a nucleophilic group and the second polysaccharide derivative is functionalized with an electrophilic group, and both the first and second precursor solutions are sterilized, (b) mixing the first precursor solution and the second precursor solution into a in situ cross-linkable mixed solution, and (c) injecting the mixed solution to a target site in a body of a patient, wherein the nucleophilic group of the first polysaccharide derivative and the electrophilic group of the second polysaccharide derivative form a covalent linkage in situ to result in the formation of a cross-linked hydrogel at the target site, wherein the first polysaccharide derivative is a hydrazide functionalized first hyaluronic acid (HA) derivative and the second polysaccharide derivative is an aldehyde functionalized second hyaluronic acid (HA) derivative, and the first HA derivative is functionalized with a hydrazide moiety at a carboxyl group of a saccharide unit of HA wherein said hydrazide moiety is hydrazide or carbodihydrazide, and the second HA derivative is functionalized with an aldehyde moiety made by conversion of a —$CH_2OH$ group into a —CHO group.

* * * * *